(12) United States Patent
Ross et al.

(10) Patent No.: US 9,622,704 B2
(45) Date of Patent: Apr. 18, 2017

(54) STRESS TEST BRA

(71) Applicants: Sheryl Ross, Santa Monica, CA (US); Jennifer Dixon, Sherman Oaks, CA (US); Jeanne Cohen, Chicago, IL (US)

(72) Inventors: Sheryl Ross, Santa Monica, CA (US); Jennifer Dixon, Sherman Oaks, CA (US); Jeanne Cohen, Chicago, IL (US)

( * ) Notice: Subject to any disclaimer, the term of this patent is extended or adjusted under 35 U.S.C. 154(b) by 0 days.

(21) Appl. No.: 15/144,691

(22) Filed: May 2, 2016

(65) Prior Publication Data
US 2016/0310075 A1    Oct. 27, 2016

Related U.S. Application Data

(63) Continuation-in-part of application No. 14/695,643, filed on Apr. 24, 2015, now Pat. No. 9,326,553.

(51) Int. Cl.
*A61B 5/00* (2006.01)
*A41C 3/00* (2006.01)
*A41C 3/02* (2006.01)
*A61B 5/0408* (2006.01)

(52) U.S. Cl.
CPC .......... *A61B 5/6804* (2013.01); *A41C 3/0064* (2013.01); *A41C 3/02* (2013.01); *A61B 5/0006* (2013.01); *A61B 5/0408* (2013.01); *A61B 5/6898* (2013.01); *A61B 2560/0468* (2013.01)

(58) Field of Classification Search
CPC ....... A41C 3/0035; A41C 3/00; A41C 3/0064; A41C 3/0057; A41C 3/005; A41D 3/0012; A41D 27/20; A41D 27/205
USPC ................. 450/89; 2/247, 250–252
See application file for complete search history.

(56) References Cited

U.S. PATENT DOCUMENTS

| | | | | |
|---|---|---|---|---|
| 1,900,129 A | * | 3/1933 | Ring ......................... | A41C 1/06 2/250 |
| 2,436,430 A | * | 2/1948 | Hart ....................... | A41C 3/0035 2/250 |
| 2,492,862 A | * | 12/1949 | Harvey ................. | A41C 3/0035 150/101 |
| 2,503,847 A | * | 4/1950 | Shanahan ............. | A41C 3/0035 224/638 |
| 2,610,325 A | * | 9/1952 | Schlussel ................. | A41C 3/00 2/247 |
| 2,624,881 A | * | 1/1953 | Lee ....................... | A41C 3/0035 2/247 |

(Continued)

OTHER PUBLICATIONS

International Search Report and Written Opinion of the International Searching Authority dated Jul. 29, 2016, in 10 pages.

*Primary Examiner* — Gloria Hale
(74) *Attorney, Agent, or Firm* — Duane Morris LLP

(57) ABSTRACT

A bra configured to provide coverage of a patient's breasts and easy deployment of at least one health parameter sensor coupled to the patient's breasts is disclosed. In one embodiment, a first cup of the bra is sized and shaped differently than a second cup of the bra so as to allow one or more sensors to contact exposed portions of the patient's breast left exposed by the first cup. In a further embodiment, the bra includes at least one pocket located on one or both cups of the bra, the at least one pocket configured to hold and secure at least one health parameter sensor configured to transmit health parameter signals to a monitoring device either via a wire or wirelessly.

19 Claims, 10 Drawing Sheets

(56) References Cited

U.S. PATENT DOCUMENTS

| | | | | |
|---|---|---|---|---|
| 4,666,432 A * | 5/1987 | McNeish | A61M 25/02 128/DIG. 26 |
| 5,496,205 A * | 3/1996 | Lee | A41C 3/0035 2/247 |
| 6,176,761 B1 * | 1/2001 | Underhill | A41C 3/0014 450/1 |
| 6,390,885 B1 * | 5/2002 | Brooks | A41C 3/0064 450/1 |
| 6,517,410 B1 * | 2/2003 | Underhill | A41C 3/0057 450/1 |
| 7,118,444 B2 * | 10/2006 | Newman | A41C 3/0028 450/54 |
| 8,597,072 B1 * | 12/2013 | Lucas | A41C 3/0035 2/247 |
| 2006/0121826 A1 * | 6/2006 | Nazzaro | A41C 3/0035 450/89 |
| 2007/0298684 A1 * | 12/2007 | Spagna | A41C 3/0035 450/89 |
| 2008/0032600 A1 * | 2/2008 | Updyke | A41C 3/0035 450/89 |
| 2008/0261489 A1 * | 10/2008 | Sweeney | A41C 3/0035 450/39 |
| 2009/0104845 A1 * | 4/2009 | Pintor | A41C 3/0035 450/31 |
| 2009/0209173 A1 * | 8/2009 | Arledge | A41C 3/0035 450/39 |
| 2010/0297913 A1 | 11/2010 | Liegey | |
| 2011/0225700 A1 * | 9/2011 | Kogut | A41B 9/001 2/113 |
| 2011/0244758 A1 * | 10/2011 | Boatright | A41C 3/0035 450/89 |
| 2012/0135667 A1 | 5/2012 | Chan | |
| 2012/0276812 A1 * | 11/2012 | Wollowick | A45F 5/02 450/89 |
| 2013/0288569 A1 * | 10/2013 | Gentry | A41C 3/12 450/86 |
| 2013/0303052 A1 * | 11/2013 | Conrad | A41C 3/0057 450/89 |
| 2013/0316616 A1 | 11/2013 | Thompson | |
| 2014/0051331 A1 * | 2/2014 | Handras | A41C 3/0035 450/89 |
| 2014/0206948 A1 * | 7/2014 | Romem | A61B 5/0022 600/301 |
| 2015/0038051 A1 | 2/2015 | Fisher et al. | |
| 2015/0099420 A1 | 4/2015 | Reinhard | |

* cited by examiner

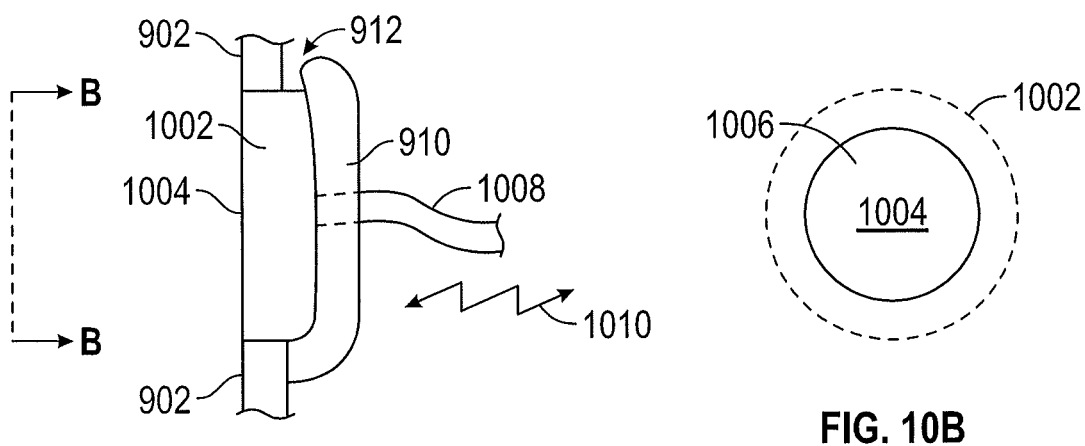
FIG. 10A
FIG. 10B
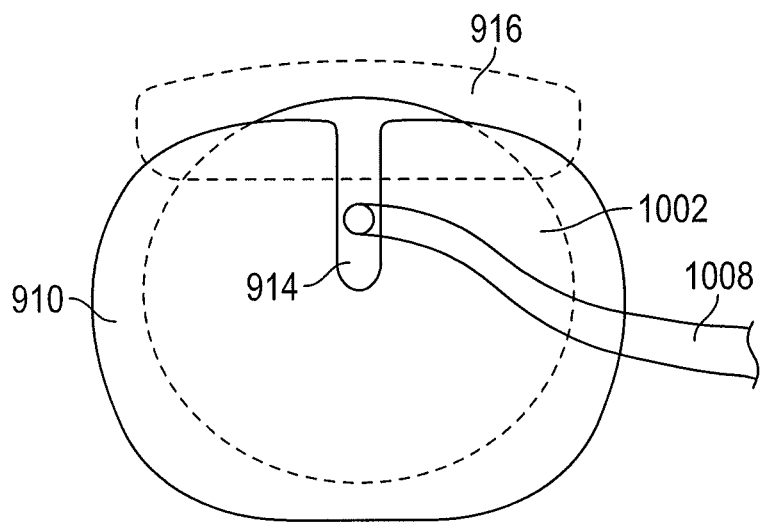
FIG. 10C

STRESS TEST BRA

CROSS-REFERENCE TO RELATED APPLICATION

The present application is a continuation-in-part of co-pending U.S. patent application Ser. No. 14/695,643, filed on Apr. 24, 2015, which is incorporated by reference herein in its entirety.

BACKGROUND

Heart disease is one of the most prevalent causes of death among women in the world and especially in the United States of America, where the disease afflicts approximately 1 in 3 women. While heart disease death rates among men have declined steadily over the last 25 years, rates among women have fallen at a far slower rate. The myth that heart disease is a "man's disease" has been debunked; the rate of public awareness of cardiovascular disease (CVD) as the leading cause of death among US women has increased from 30% in 1997 to 54% in 2009. Despite gains in diagnosis and treatment, considerable challenges remain.

In 2007, CVD still caused 1 death per minute among women in the United States, or over 400,000 deaths that year. More women were killed by CVD than cancer, chronic lower respiratory disease, Alzheimer disease, and accidents combined. Reversing a trend of the past decades, CVD death rates in US women 35 to 54 years of age now actually appear to be increasing, likely because of the effects of the obesity epidemic. The situation is worse for black and Hispanics females compared to their Caucasian counterparts. A very ominous trend is the ongoing increase in average body weight in the former populations, with nearly 2 of every 3 of those women over 20 years of age now being overweight or obese.

The rise in obesity is a key contributor to the burgeoning epidemic of type 2 diabetes mellitus now seen in 12 million US women. The increasing prevalence of diabetes mellitus is concerning for many reasons, especially for its association with a greatly increased overall risk of myocardial infarction (MI), CVD, and stroke. The challenge of these diseases in women is not limited to the United States. Recent data document the global scope of the problem: Heart disease (CVD) is the leading cause of death in women in every major developed country and most emerging economies. One of the most effective tools to diagnose and therefore lead to treatment of these ailments is an echocardiogram test.

An echocardiogram test is a test that uses ultrasound (sound waves) to create images of the heart. In principle, sound waves are provided to a patient's internal body through a transducer being moved over the patient's chest, sound waves reflected from an internal body structure (e.g., a heart) are to be captured by the transducer, and such sound waves reflected from the heart may be re-constructed to create an image of the heart. Generally, the echocardiogram test includes three steps. The first step of the echocardiogram test is referred to as a "resting echocardiogram test" and is directed to using the sound waves to create the patient's heart image when the patient is at rest.

The second step of the echocardiogram test is referred to as an "exercise stress test," or a "stress electrocardiogram test." Generally, the exercise stress test follows the resting echocardiogram test and uses an electrocardiogram (EKG or ECG) pad to record the patient's heart's electrical activity while the patient is performing an exercise. A typical exercise stress test involves having the patient run on a treadmill, step on an elliptical machine, or bike on a stationary bicycle for a period of time (e.g., 6 to 10 minutes) while one or more EKG pads are placed on the patient's upper body such that the patient's heart's electrical activity can be measured by the EKG pad.

After the exercise stress test, the third step of the stress echocardiogram test, referred to herein as a "post-exercise echocardiogram test," is generally performed. During the post-exercise echocardiogram test, the transducer is moved over the patient's chest to create the heart image right after the patient stops exercising, in accordance with some embodiments. Different from the resting echocardiogram test, the post-exercise echocardiogram test is directed to creating the heart's image while the heart is not at rest. The resting echocardiogram test and post-exercise echocardiogram test preferably are performed within seconds or minutes from the exercise stress test for accurate assessment, for example by moving the patient onto an examination table where a technician is able to access the patient's beating heart with the ultrasound transducer in specific places. Thus, quick and easy access to the patient's left breast is beneficial for accurate results since the heart is located on the left side of the upper chest.

One problem with the exercise stress test is that patients are usually requested to run on a treadmill at steep inclines without any supportive and/or protective clothing on their upper torso. The primary reason for this request is that such conventional clothing may interfere with application of diagnostic instruments such as EKG sensors and leads and/or sonogram transducer sensors. This requirement may be both physically and emotionally uncomfortable for female patients, resulting in hesitancy to undergo a stress test. In addition, a woman may not exert maximum effort during the test due to the lack of supportive and/or protective clothing for her breasts.

Physically, when a woman runs on a treadmill without any garment (e.g., a bra) on her upper torso, her breasts may move in an uncomfortable and painful manner. This may create physical duress (i.e., pain). Emotionally, women may be uncomfortable running on a treadmill without clothing on their upper torsos while others are present, let alone running with maximal effort. These physical and emotional considerations may discourage women from undergoing a stress test. Furthermore, even if a woman chooses to undergo a stress test, her physical and emotional discomfort may actually unduly influence (e.g., extenuate increased hear rate, respiration and/or blood pressure) the stress test results and decrease the test's diagnostic efficacy.

Additionally, while performing the exercise stress test, a patient is required to be attached a plurality of EKG pads (e.g., typically nine or more) at least over the patient's upper body. A physician/doctor attaches the plurality of EKG pads to the patient's skin, which typically requires the physician/doctor to have a direct physical contact with the patient's upper body, especially around the breast area. In one aspect, such physical contact may cause physical and/or emotional discomfort to the patient. In another aspect, a female patient may wear an apparel to cover her upper body while undergoing the stress exercise test. The plural EKG pads are typically deployed beneath and/or around the apparel, which may accordingly cause some interference between the EKG pads and the apparel. Typically, the plurality of EKG pads are typically connected to a monitoring machine (e.g., a monitoring machine used to process the recorded heart's electrical activity) through a plurality of electrical wires or cables. Such a plurality of wires may disadvantageously cause a variety of problems such as, for example, tangling of the wires, accidental dragging of the monitoring machine, etc., while the patient is exercising.

BRIEF DESCRIPTION OF THE DRAWINGS

Aspects of the present disclosure are best understood from the following detailed description when read with the accompanying figures. It is noted that various features are not necessarily drawn to scale. In fact, the dimensions of the various features may be arbitrarily increased or reduced for clarity of discussion.

FIG. 10A illustrates a cross-sectional view of a pocket of the bra of FIG. 9 in accordance with some embodiments.

FIG. 10B illustrates a front view of the pocket of the bra of FIG. 10A in accordance with some embodiments.

FIG. 10C illustrates a back view of the pocket of the bra of FIG. 10A in accordance with some embodiments.

DETAILED DESCRIPTION OF EXEMPLARY EMBODIMENTS

The following disclosure describes various exemplary embodiments for implementing different features of the subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Additionally, it will be understood that when an element is referred to as being "connected to" or "coupled to" another element, it may be directly connected to or coupled to the other element, or one or more intervening elements may be present.

In some embodiments of the invention, a bra includes two cups for breasts, with at least one of the cups being detachably securable, and a retaining band. The retaining band keeps one of the cups (e.g., the right cup) at least partially in proper anatomical position on a wearer of the bra while the other cup is not secured. In some embodiments, the retaining band also is detachably securable and/or forms at least part of one of the cups.

In further embodiments, a bra may include at least one pocket in at least one of the cups for securing at least one health parameter sensor, which may be either wired or wireless-enabled to communicate with a health monitoring system or device, as discussed in further detail below. In embodiments where the health parameter sensors are wireless-enabled, the need for plural electrical wires that are required for conventionally wired health parameter sensors can be advantageously eliminated.

In alternative embodiments, a health-monitoring bra need not include a retaining band such that the left cup, for example, includes only a single piece of fabric to cover and support the left breast of a patient. In further embodiments, the left cup is sized and shaped differently than a right cup of the bra so as to allow one or more sensors to easily contact portions of the patient's left breast that remain exposed by the left cup, without interference from the bra material.

Figure 1:
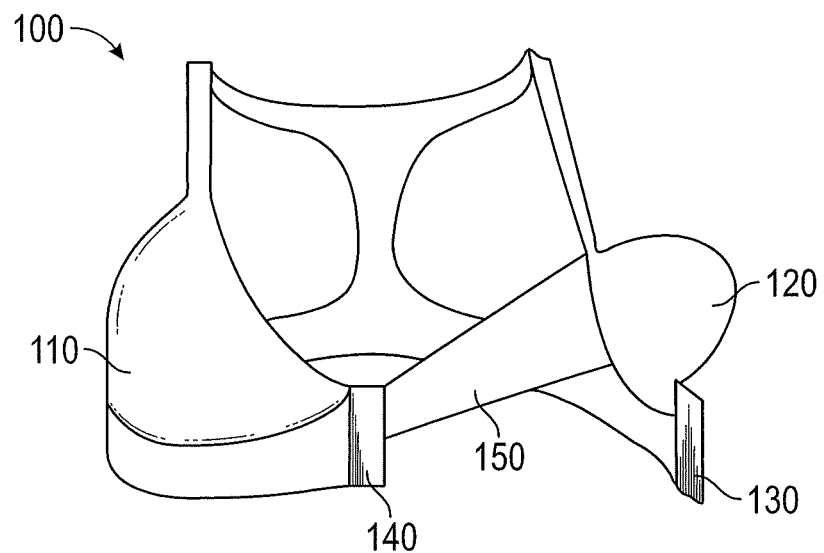
FIG. 1 illustrates an example of a bra in accordance with some embodiments.

FIG. 1 illustrates an example of a bra according to some embodiments of the present disclosure. Bra 100 includes cups 110, 120, and a retaining band 150. The cup 110 is configured to cover at least a portion of a wearer's right breast, and the cup 120 is configured to cover at least a portion of a wearer's left breast. At least one of the cups, hereinafter the "left cup" 120, is detachably securable for example via hook-and-loop fasteners 130 and 140. Other types of fasteners such as buttons, laces, and the like may also be used. According to some embodiments, when the left cup 120 is attached to the cup 110, hereinafter "right cup," the retaining band 150 is disposed under and concealed by the left cup 120, as shown in the closed configuration of the bra of FIG. 3.

Figure 3:
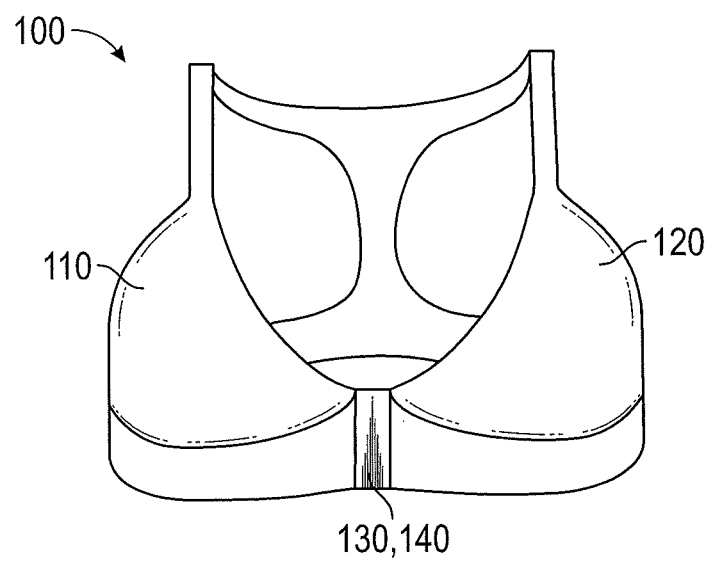
FIG. 3 illustrates an example of the bras shown in FIGS. 1 and 2 in a closed configuration in accordance with some embodiments.

In the illustrated embodiment of FIG. 3 in which the bra is in the closed configuration, at least portions of the wearer's right and left breasts are covered by the right cup 110 and the left cup 120, respectively. Referring back to FIG. 1, in accordance with some embodiments, when the left cup 120 is detached from the right cup 110, the retaining band 150 can still cover at least a portion of the left breast. As such, the retaining band 150 provides at least some coverage of a woman's breast to decrease potentially emotional and physical discomfort.

Figure 2:
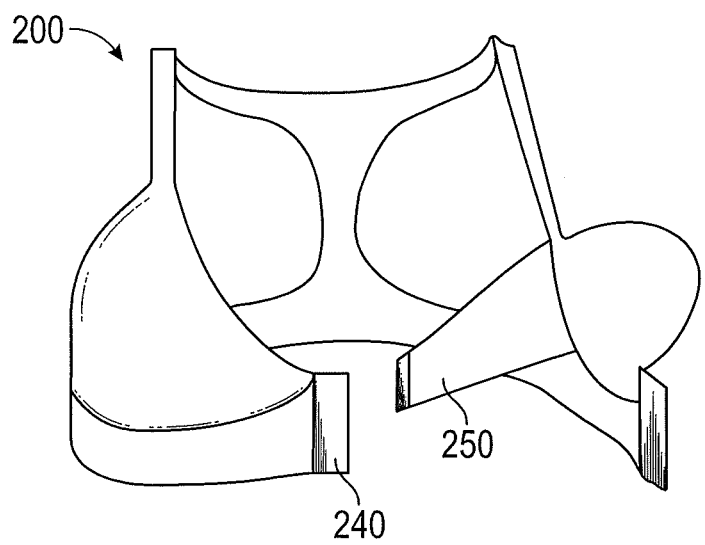
FIG. 2 illustrates an example of a variation of the bra of FIG. 1 in accordance with some embodiments.

FIG. 2 illustrates an example of a variation of the bra shown in FIG. 1. Bra 200 in FIG. 2 includes the feature that retaining band 250 also is detachably securable, for example, also via a hook-and-loop 240 or other type of fastener. In some embodiments, if a patient has had a mastectomy wherein one or both breasts are removed, one or both cups of the bra 100 or 200 may be omitted and replaced by a corresponding retaining band 150 or 250.

FIG. 3 illustrates a closed configuration of the bra 100 in accordance with various embodiments. As shown, when the bra 100 is in the closed configuration, the left cup 120 is attached to the right cup 110 and the retaining band 150 is disposed under and concealed by the left cup 120. More particularly in the illustrated embodiment of FIG. 3, when the bra 100 is in the closed configuration, the hook-and-loop fasteners 130 and 140 are overlapped and attached to each other.

Figure 4:
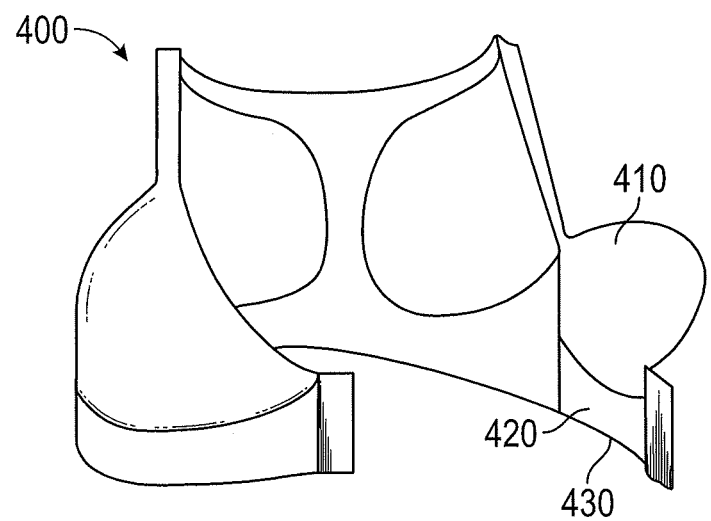
FIG. 4 illustrates another example of a variation of the bra of FIG. 1 in accordance with some embodiments.

FIG. 4 illustrates another example of a variation of the bra shown in FIG. 1. Example bra 400 in FIG. 4 is identical to bra 100 in FIG. 1 except that the retaining band is at least partly formed by cup 410. That cup (i.e., 410) includes a window 420 with bottom edge or pane that provides a bottom edge 430 of the window 420. In accordance with some embodiments, the window 420 allows EKG electrodes, leads, and wires, ultrasound instruments, sonography devices, and/or other diagnostic instruments to pass therethrough while allowing the cup portion 410 to cover at least a portion of the patient's breast during testing.

Figure 5:
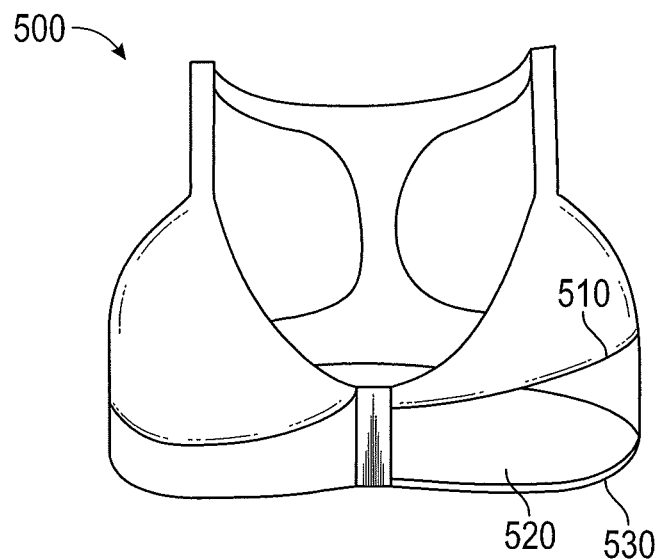
FIG. 5 illustrates an example of the bra shown in FIG. 4 in a closed configuration in accordance with some embodiments.

FIG. 5 illustrates an example of the bra shown in FIG. 4 in a closed configuration. Bra 500 in FIG. 5 illustrates window 520 that corresponds to window 420 in FIG. 4 with bottom edge 530 that corresponds to bottom edge 430 in FIG. 4.

In the illustrated embodiments of FIGS. 4 and 5, windows 420 and/or 520 are preferably curved upward on the outer side of the cup 410/510 to facilitate deployment of EKG leads and/or a sonography device or other instrument during a stress test. As such, an EKG lead, a sonography device, and/or other instrument may be allowed to deploy on a wearer's skin (e.g., breasts) through a curved upward top edge 510 of the cup 510 more conveniently. In some aspects, the window provides a passage for the leads and associated wires as well as for ultrasound examination once the target heart rate has been achieved.

Figure 6:
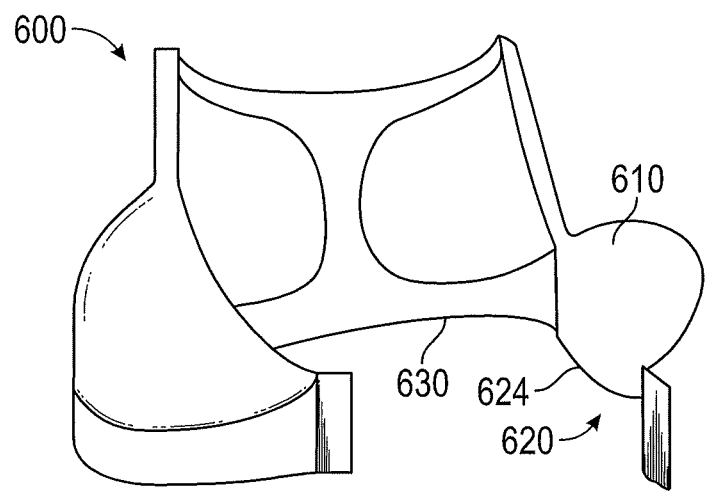
FIG. 6 illustrates an example of a variation of the bra of FIG. 4 in accordance with some embodiments.

FIG. 6 illustrates an example of a variation of the bra shown in FIG. 4. In example 600 shown in FIG. 6, a window 620 is open on a bottom edge (e.g., does not include a bottom edge such as edges 430 and 530 shown in FIGS. 4 and 5, respectively). The bottom edge is omitted in this example to help avoid rubbing of the bra on EKG sensors and/or leads, which could cause artifacts such as false positive results. In some embodiments, the top edge 624 of the window 620 (i.e., also the bottom edge of the cup 610) may be aligned with and meet a bottom edge 630 of a back portion 632 of the bra so that cup 610 is secured to the back portion 632 (e.g., a bottom back strap 632) of the bra 600. Thus, no part of the bra is unsecured.

Figure 7:
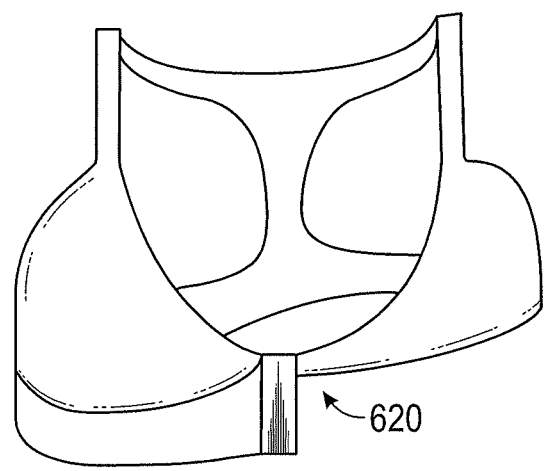
FIG. 7 illustrates an example of the bra shown in FIG. 6 in a closed configuration in accordance with some embodiments.

FIG. 7 illustrates an example of the bra shown in FIG. 6 in a closed configuration.

Figure 8:
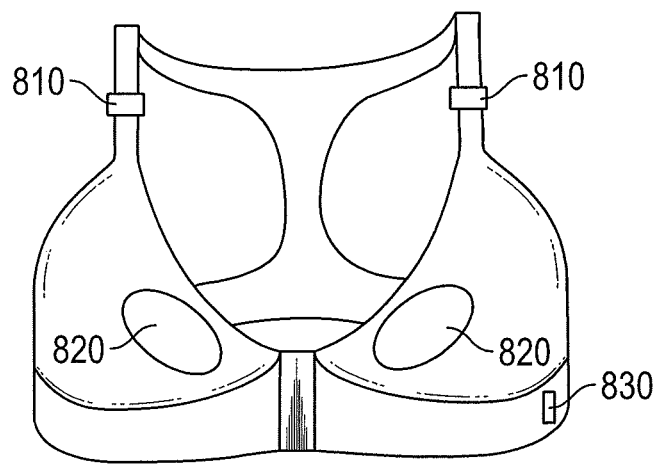
FIG. 8 illustrates an example of the bra of FIG. 1 including one or more additional features in accordance with some embodiments.

FIG. 8 illustrates possible additional features according to aspects of the subject technology. One or more strap adjusters 810 may be included to help with proper fitting of the bra. One or more windows 820 in a "heart side" of one or more of the cups (i.e., near the center of the bra when in a closed position) may also be included to facilitate access of a sonogram or other sensor or imaging device. In addition, one or more clasps 830 to hold test (e.g., EKG electrode) leads may be included. The clasp(s) may be hook-and-loop fastener loops or any other type of clasp(s) that preferably secure the leads in place without undue wear or interference.

Figure 9:
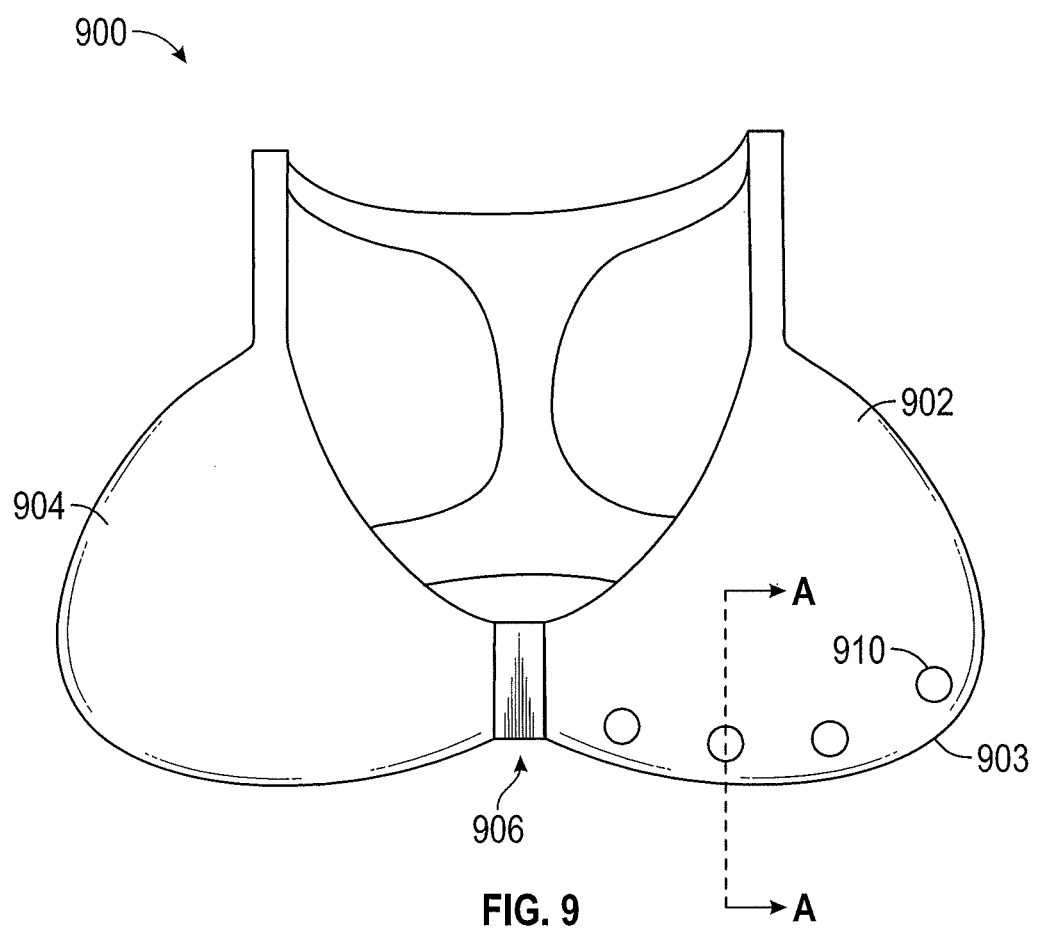
FIG. 9 illustrates an example of a bra that includes one or more pockets for housing EKG pads in accordance with some embodiments.

FIG. 9 illustrates a perspective front view of a bra 900 that includes one or more pockets in at least one of the cups of the bra 900, in accordance with some embodiments. As shown in the illustrated embodiment of FIG. 9, the bra 900 includes a left cup 902 and a right cup 904, and the bra 900 is in the closed configuration, i.e., the left cup 902 and the right cup 904 are attached together through a fastener 906. A variety of fasteners 906 may be used to attach one of the cups to the other such as, for example, a hook-and-loop fastener, a magnetic fastener, etc.

In the illustrated embodiment of FIG. 9, the left cup 902 includes four pockets 910. Each pocket 910 is configured to house and secure an EKG pad. Further details of the pockets 910 will be provided in the cross-sectional views of the bra 900 in FIGS. 10 and 11. Although in the illustrated embodiment of FIG. 9, four pockets in the left cup are illustrated, any number of pockets may be included in any one or both of the cups while remaining within the scope of the present disclosure. For example, the left cup 902 may include six pockets and/or the right cup 904 may include six pockets. Additionally, in FIG. 9, the pockets 910 are deployed around a lower edge 903 of the left cup 902. However, the pockets 910 may be deployed in any of a variety of locations of the cup as long as the location of the pocket is suitable for housing and securing an EKG pad for monitoring a desired location on the patient. In some embodiments, the pocket 910 may be implemented as any of a variety of shapes, for example, a square, a circle, a triangle, and etc. In some embodiments, the pocket 910 may have a dimension that is suitable for housing and securing an EKG pad, for example, or type of sensor. In one embodiment, the pocket 910 is about 4 centimeters in diameter or width.

In general, a body sensor pad is an electrode or a pad attached to a patient's body that is used to record the patient's biopotential signals or health parameters. An EKG pad is one of a variety of body sensors that is used to record the electrical activity of the patient's heart. By deploying one or more EKG pads over a specific location of the patient's body (e.g., the chest), the patient's heart's electrical activity can be measured/recorded by the deployed EKG pad and the measured electrical activity may be displayed as a series of tracing data over time by a monitoring machine that is coupled to the EKG pads either via wires and/or via a wireless communication link (e.g., Bluetooth), as described in further detail below. The tracing data may indicate one or more heart-related conditions, and a doctor/physician may determine whether an irregular heart condition exists based on the tracing data.

As discussed above, in order to prevent any physical and/or emotional discomfort for a patient while the patient undergoes a stress exercise test, the patient generally wears an apparel to cover his or her upper body. Conventionally, such apparel may cause some interference with EKG pads, especially while exercising. Thus, some embodiments of the present disclosure provide various advantages over the conventional art by using the bra 900 that includes one or more pockets to house and secure EKG pads. As such, when the patient wearing the bra 900 undergoes the stress exercise test discussed above, for example, one or more EKG pads contained in the pocket(s) 910 of the bra 900 can record the patient's heart activity, while the bra 900 also serves to provide support and concealment of the patient's breasts during the exercise.

Exemplary embodiments of the pockets 910 are discussed in further detail below. In the following discussion, although the pocket of the bra is directed to house and secure an EKG pad that is configured to record the electrical activity of the patient's heart, any type of a variety of sensors that are used to record the patient's health parameters may be housed and secured in the pocket while remaining within the scope of the present disclosure. In some embodiments, the bra 900 does not include a retaining band 150 as discussed above with respect to FIG. 1. Thus, the left cup 902 comprises a single piece of fabric to cover the patient's left breast.

FIG. 10A illustrates a cross-sectional view of the pocket 910 of the left cup 902 along line A-A of FIG. 9, in accordance with some embodiments. FIG. 10B illustrates a perspective back view of the pocket 910 of FIG. 10A taken along line B-B of FIG. 10A, in accordance with some embodiments. FIG. 10C illustrates a perspective front view of the pocket 910 of FIG. 10A, in accordance with some embodiments. The following discussion references FIGS. 10A, 10B and 10C.

As shown in the cross-sectional view of FIG. 10A, the pocket 910 has an opening 912 at the top of the pocket 910 through which the sensor 1002 may be inserted into the pocket 910. The pocket 910 may be attached to the cup 902 by any known means such as, for example, sewing left, right and bottom edges of the pocket 910 to the material of the bra cup 902, while leaving the top of the pocket 910 open to form opening 912 that allows the sensor 1002 to be placed inside and secured within the pocket 910. In some embodiments, at least a portion or all of a back surface 1004 of the sensor 1002 may be exposed through a hole or window 1006 (FIG. 10B) in the material of bra cup 902 to allow for direct contact between the back surface 1004 and the skin of a patient's breast.

In one embodiment, the sensor 1002 has a wire 1008 that extends out from the sensor 1002 through a slot 914 (FIG. 10C). The wire 1008 is configured to transmit measured health parameter signals from the sensor 1002 to a signal monitoring or processing system. In one embodiment, the sensor 1002 is an EKG pad and the wire 1008 transmits data concerning electrical activity of a patient's heart to an EKG monitoring machine, as described in further detail below. Examples of the electrical wire 1008 may include an USB cable, an Ethernet cable, an optical fiber cable, and/or any of a variety of wires/cables that are suitable for transmitting data. Such electrical wire 1008 may be further configured to power the sensor 1002, or in some other embodiments, the sensor 1002 may be powered by a battery, through another electrical wire, through solar energy, etc., while remaining within the scope of the present disclosure.

In some embodiments, the sensor 1002 is wireless-enabled so that instead of using an electrical wire 1008 to communicate with a monitoring machine, the sensor 1002 may utilize a wireless communication link 1010 to communicate with a monitoring machine and/or a portable processing device (e.g., a smart phone or tablet device), as described in further detail below in connection with FIG. 15. In such embodiments, the communication link 1010 may utilize any suitable known wireless communication protocol, such as but not limited to, Wi-Fi, Bluetooth Low Energy (BLE), Worldwide Interoperability for Microwave Access (Wi-MAX), etc. Wireless sensors, such as wireless EKG sensors, are known in the art. For example, a wireless EKG sensor sold as CardioSecur ACTIVE is provided by CardioSecur, Inc. Another wireless EKG sensor sold as Kardia is provided by AliveCor, Inc. Wireless EKG monitors are also known, and provided, for example, by iHealth, Inc.

Referring again to FIG. 10C, the front view of the pocket 910 and a secured sensor 1002 are shown in accordance with various embodiments. The pocket 910 may optionally include a top cover or flap 916 that can be sewn onto the bra cup 902 material above the opening 912 of the pocket 910. After insertion of a sensor 1002 into the pocket 910, the top flap 916 may be closed over the sensor 1002 to further secure the sensor 1002 within the pocket 910. The top flap 916 may be closed and detachably secured to a top portion of the pocket 910 by any known means such as, for example, one or more buttons, hook-and-loop fasteners (a.k.a., "velcro"), etc.

In accordance with various embodiments, the sensor 1002 comprises an EKG pad having a surface (e.g., back surface 1004) that is in direct contact with the skin. In such embodiments, the EKG pad 1002 may be attached to the skin via a conductive adhesive layer (glue), which is generally referred to as a "wet contact" EKG pad. Alternatively, some EKG pads are configured to contact a patient's skin without such an adhesive layer, and are generally referred to as "dry contact" EKG pads. In some other embodiments, the EKG pad 1002 need not be in direct contact with the wearer's skin and the window 1006 (FIG. 10B) may be unnecessary. Such an EKG pad 1002 may use a capacitive coupling through an insulator between the EKG pad 1002 and the skin, wherein the EKG pad may capture the heart's electrical activity through the capacitive coupling. Generally, such EKG pads with the capacitive coupling are able to measure electrical potential on the skin without requiring resistive electrical contact with the patient's skin.

Figure 11A:
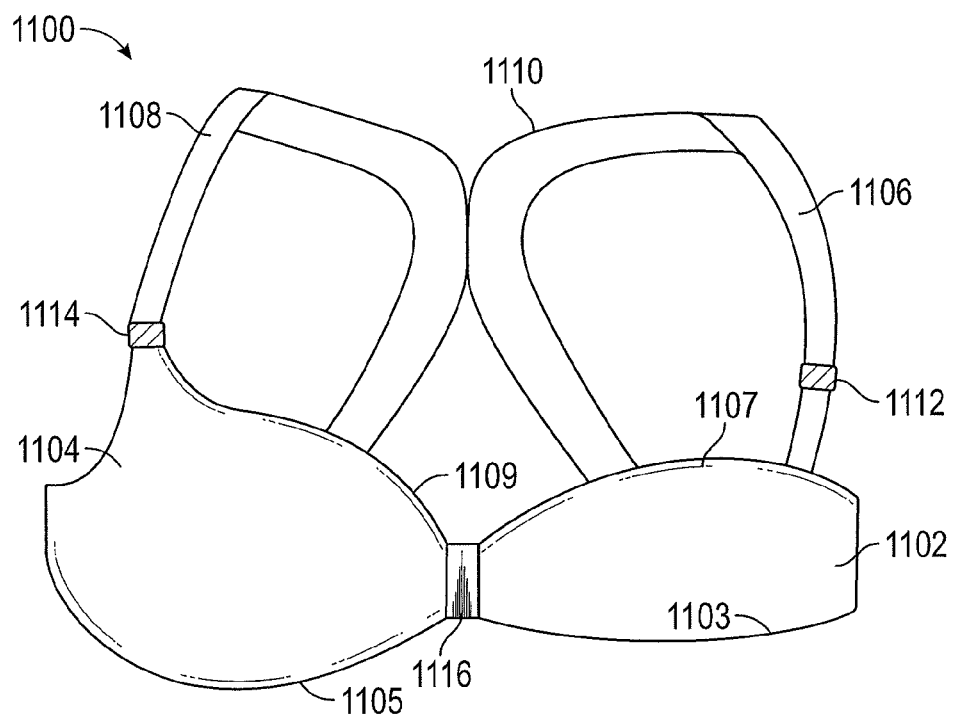
FIG. 11A illustrates a front view of an example of a one-piece bra in accordance with some embodiments.
Figure 11B:
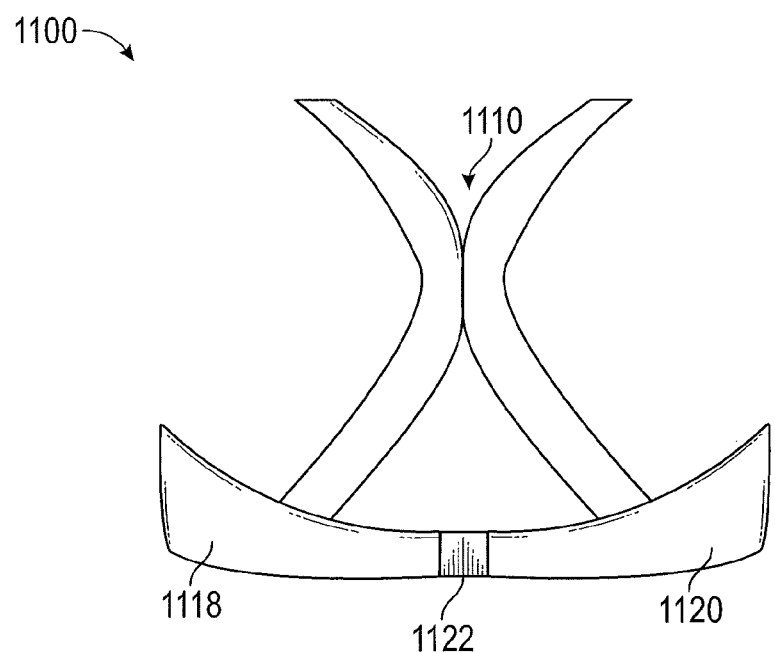
FIG. 11B illustrates a rear view of the example of the one-piece bra of FIG. 11A in accordance with some embodiments.

FIGS. 11A and 11B, respectively, illustrate front and rear perspective views of a bra 1100 that includes two cups sized and shaped differently from each other, in accordance with some embodiments of the invention. Referring first to the embodiment of FIG. 11A, the bra 1100 includes a left cup 1102 that is made from a single piece of fabric (i.e., no retaining band 150) and configured to cover at least part of the left breast of the wearer, a right cup 1104 configured to cover the right breast of the wearer, a left strap 1106, a right strap 1108, a left adjuster 1112, a right adjuster 1114, an upper back support portion 1110, and a front fastener 1116. Each of these features of the bra 1100 are discussed in further detail below.

Referring now to the embodiment of FIG. 11B, the bra 1100 further includes a rear fastener 1122, and lower back support portions 1118 and 1120 from which the upper back support portion 1110 extends. In FIGS. 11A and 11B, the bra 1100 is in a closed configuration, i.e., the left cup 1102 and the right cup 1104 are attached together through the front fastener 1106, and the lower back portions 1118 and 1120 are attached together through the rear fastener 1122. A variety of types of known fasteners can be used for fasteners 1106 and 1122 to attach the left and right cups, or the back portions, together such as, for example, hook-and-loop fasteners, magnetic fasteners, etc.

Referring again to FIG. 11A, the left cup 1102 and the right cup 1104 of the bra 1100 may each include lower edges, 1103 and 1105, respectively, and top edges 1107 and 1109, respectively. In some embodiments, the edge 1103 may be designed to be higher than the edge 1105, as shown. As such, while the patient wears the bra 1100, a lower portion of the wearer's left breast may be exposed which may provide advantages for easier attachment of EKG pads to the lower portion of the wearer's left breast. Similarly, in some embodiments, the top edge 1107 of the left cup 1102 is lower than the top edge 1109 of the right cup 1104 to allow for easier placement of one or more sensors on an exposed upper portion of the patient's left breast. As such, the left cup 1102 is sized and shaped differently from the right cup 1104. Although, the left cup 1102 is smaller than the right cup 1104 in the embodiment illustrated in FIG. 11A, in alternative embodiments, the right cup 1104 may be formed in similar fashion such that the bottom and/or top edges 1105 and 1109 may be made to expose corresponding portions of a patient's right breast either alternatively or additionally to the exposed portions of the patient's left breast.

Figure 12A:
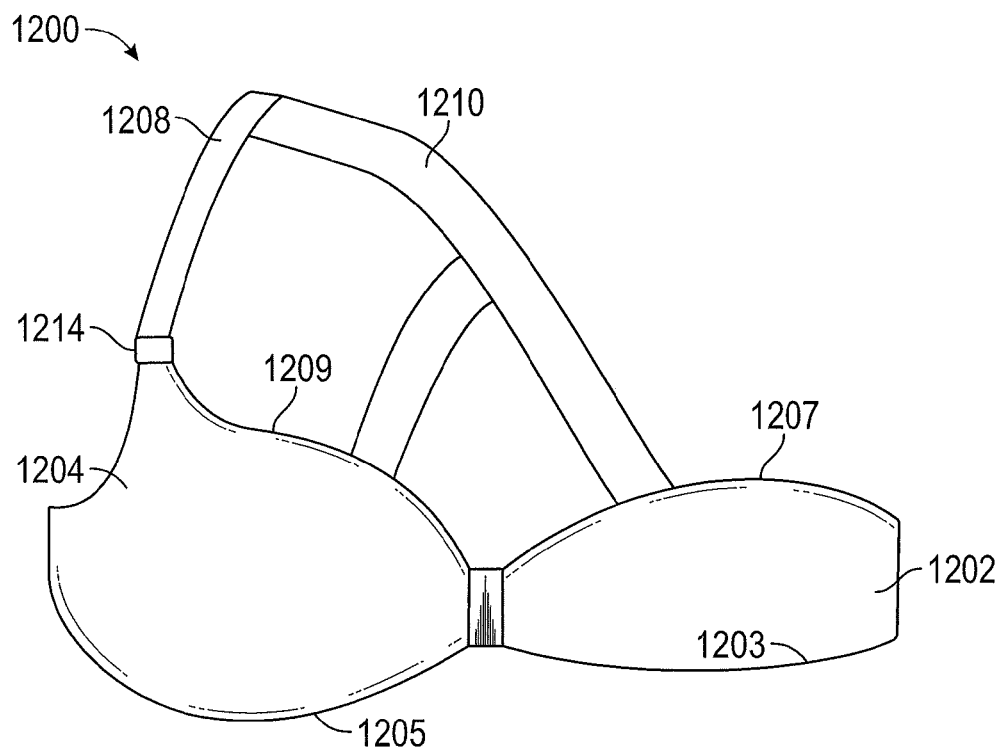
FIG. 12A illustrates a front view of an example of a one-piece bra without a left strap in accordance with some embodiments.
Figure 12B:
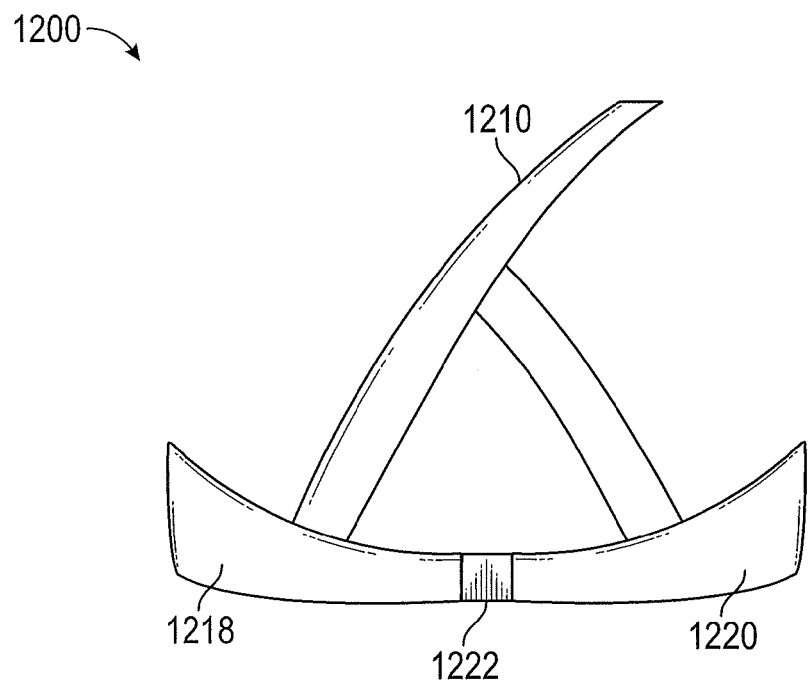
FIG. 12B illustrates a rear view of the example of the one-piece bra of FIG. 12A in accordance with some embodiments.

FIGS. 12A and 12B illustrate perspective front and rear views of a bra 1200 including two cups that are sized and shaped differently from each other, respectively, in accordance with some embodiments of the invention. The bra 1200 is substantially similar to the bra 1100 described above, except bra 1200 does not have a left strap, as described if further detail below. Referring first to FIG. 12A, the bra 1200 includes a left cup 1202 that is configured to cover at least part of the left breast of the wearer, a right cup 1204, a right strap 1208, a right adjuster 1214, an upper back support portion 1210, and a front fastener 1216. Similar to the lower edge 1103 and top edge 1107 of bra 1100, lower edge 1203 and top edge 1207 of the left cup 1202 is raised and lowered, respectively, to allow sensors such as an EKG pad to be more easily attached to exposed portions of a patient's left breast.

Referring now to FIG. 12B, the bra 1200 further includes a rear fastener 1222, and lower back support portions 1218 and 1220 from which the upper back support portion 1210 extends. In FIGS. 12A and 12B, the bra 1200 is in a closed configuration, i.e., the left cup 1202 and the right cup 1204 are attached together by the front fastener 1216, and the lower back portions 1218 and 1220 are attached together by the rear fastener 1222. A variety of fastener types may be used such as, for example, hook-and-loop fasteners, magnetic fasteners, etc.

The description of features of bra 1200 that are similar to corresponding features of bra 1100 are not repeated here. As mentioned above, one difference between bra 1200 and bra 1100 is that bra 1200 does not have a left shoulder strap and corresponding adjuster that attaches the upper back support portion 1210 to the left cup, in accordance with some embodiments. One advantage of a "strapless" left cup 1202 is that the left cup may be easier for a wearer to put on and/or take off, especially when the wearer is undergoing the stress exercise test. This is because, generally, when a patient is undergoing the stress exercise test, one or more EKG pads are attached to the patient's left breast, the absence of the left should strap may further avoid interference that may occur between a left shoulder strap and the EKG pads and/or wires of the EKG pads for wired sensor embodiments.

Figure 13:
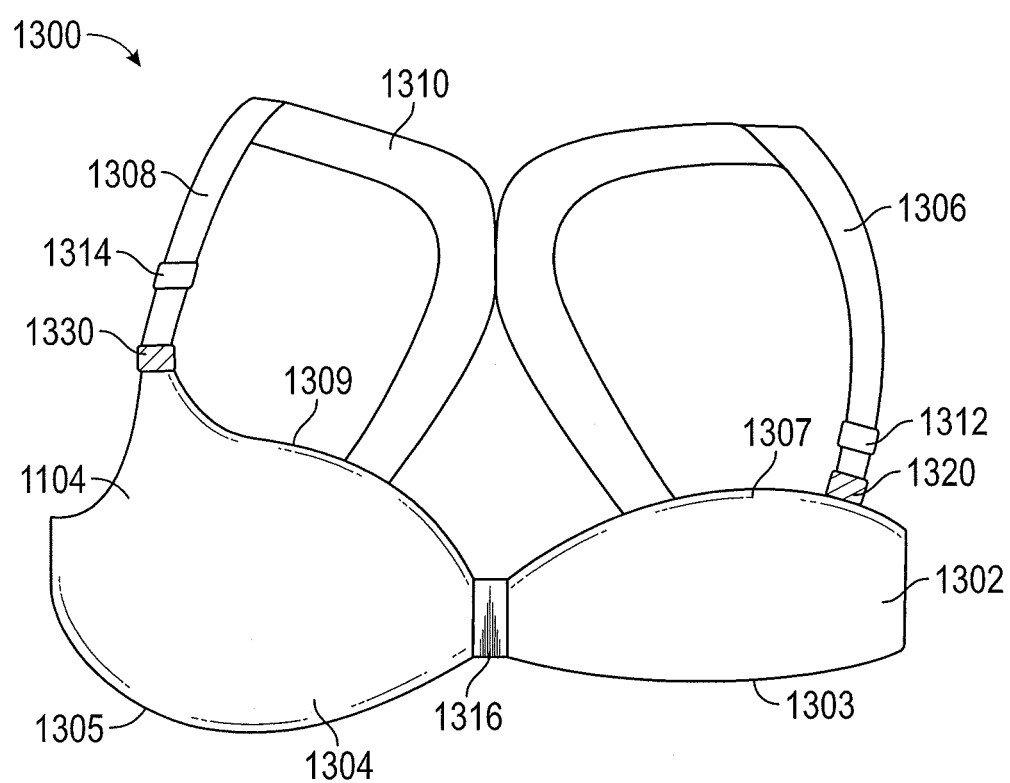
FIG. 13 illustrates a front view of an example of a one-piece bra that includes one or more left/right fasteners in accordance with some embodiments.

FIG. 13 illustrates a bra 1300 that is similar to the bra 1100 discussed above but further includes a left strap fastener 1320 and a right strap fastener 1330. The bra 1300 includes a single piece left cup 1302 that is configured to cover at least a portion of the left breast of the wearer, a right cup 1304, a left strap 1306, a right strap 1308, a left adjuster 1312, a right adjuster 1314, an upper back support portion 1310, and a front fastener 1316. Similar to bra 1100, the left cup 1302 of bra 1300 is relatively smaller than the right cup 1304 and has a relatively higher bottom edge 1303 and a lower top edge 1307 compare to corresponding edges 1305 and 1309 of the right cup 1304. Similar to the functionality of the front fastener 1316, the left and right strap fasteners 1320 and 1330 are configured to attach the left cup 1302 and the right cup 1304 to the left strap 1306 and the right strap 1308, respectively. A variety of fastener types may be used such as, for example, hook-and-loop fasteners, magnetic fasteners, etc. Such additional fasteners 1320 and 1330 may provide a variety of advantages to a wearer of the bra 1300. For example, if a wearer wants to remove the left cup 1302 quickly, the wearer may simply disengage the fastener 1320 and the fastener 1316.

Figure 14:
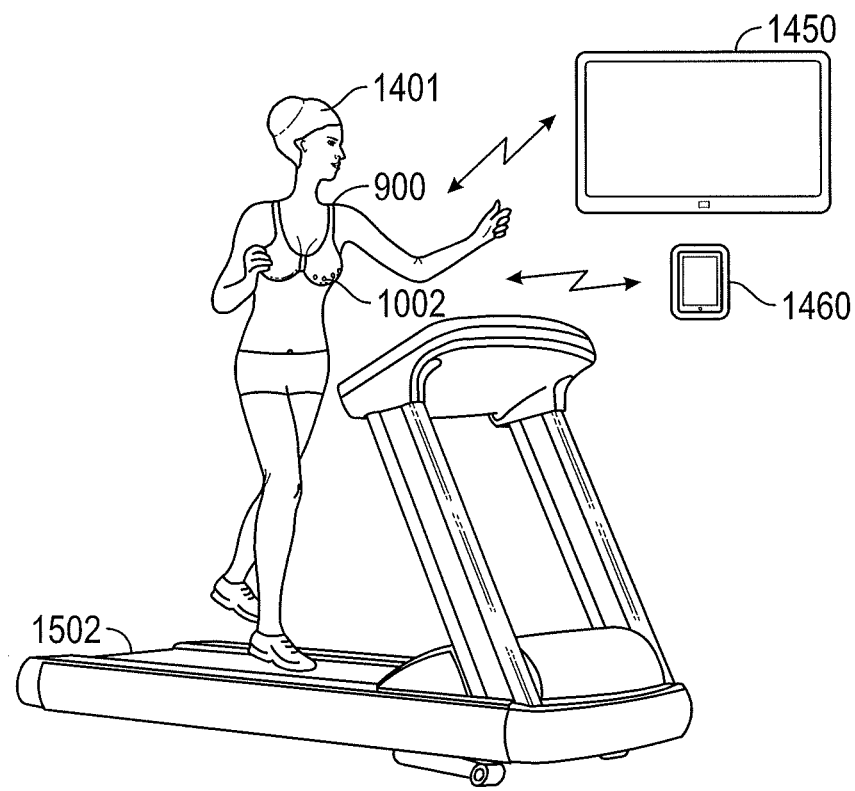
FIG. 14 illustrates an exemplary diagram in which a patient who wears the bra of FIG. 9 undergoes a stress exercise test in accordance with some embodiments.

FIG. 14 is an exemplary diagram illustrating a patient wearing a bra that includes a wireless-enabled sensor 1002 (e.g., an EKG pad) while undergoing a stress exercise test, for example, in accordance with some embodiments. As discussed above, the stress exercise test requires one or more EKG pads attached to the patient's chest to record the patient's heart electrical activity while the patient is running or walking on a treadmill. In the illustrated embodiment of FIG. 14, a patient 1401 who wears the bra 900 that includes at least one pocket 910 configured to house and secure a wireless-enabled EKG pad 1002 while running on a treadmill 1402. In alternative embodiments, the treadmill 1402 may be replaced by any other type of stationary exercise apparatus such as a stationary bicycle, an elliptical machine, a step climber, etc. By wearing such a bra that includes the wireless-enabled EKG pad 1002, the patient may advantageously avoid the hassle of tangling wires, as described above, while still enabling a monitoring machine 1450 to receive data (e.g., the patient's heart electrical activity) from the EKG pad 1002.

In some embodiments, the monitoring machine 1450 is a conventional EKG monitoring machine that is configured to receive data (e.g., the heart's electrical activity) provided by the EKG pad, either via wires or wirelessly. After receiving the measured data from one or more EKG pads, the monitoring machine 1450 processes the data to display or provide health information to a physician and/or other health care provider, in order to determine whether an irregular heart condition exists. In alternative embodiments, in addition or alternatively to the monitoring machine 1450, the wireless-enabled EKG pad 1002 may be configured to wirelessly communicate with a portable device 1460. Such a portable device 1460 may be a portable data processing device having a display screen (e.g., a smart phone, a tablet, a laptop computer, etc.) that can receive signals from one or more wireless sensors, process such signals and thereafter display data, graphs or other health-related information based on the signals received from the sensors. In some embodiments, such a portable data processing device 1460, can be programmed to perform the same data processing functions of a conventional EKG monitoring machine, for example, or other desired monitoring systems, based on wireless signals received from the wireless sensors.

Figure 15:
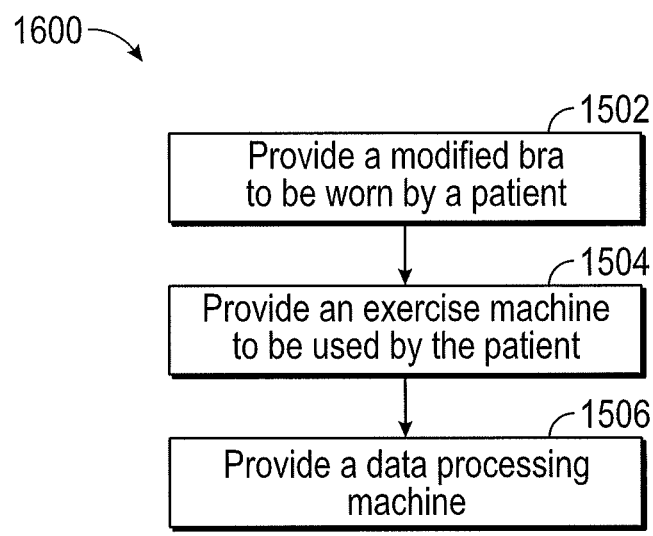
FIG. 15 illustrates an exemplary flow chart of a method for performing a stress test for a patient in accordance with some embodiments.

FIG. 15 illustrates a flow chart of a method 1500 of performing a stress test for a patient in accordance with various embodiments. The method 1500 starts with step 1502 in which the patient is provided with a modified bra to be worn. In accordance with various embodiments, the modified bra may be the same as or have features similar to any of one of the bras illustrated in FIGS. 1-13 discussed above, or any combination of such features, for providing easy deployment of one or more sensors on a patient's breasts while providing coverage and support of the patient's breasts during exercising.

The method 1500 continues to step 1504 in which an exercise machine to be used by the patient is provided. In some embodiments, the exercise machine can be any one of a treadmill, a stationary bike, and an elliptical machine, for example.

Next, at step 1506, a data processing machine is provided and communicatively coupled to the one or more sensors. In accordance with various embodiments of the present disclosure, the data processing machine is configured to receive and process health parameter signals from the sensor(s) while the patient is exercising on the exercise machine. In some embodiments, the data processing machine may be a conventional EKG monitoring machine. In alternative embodiments, the data processing machine can be a portable data processing device having a display screen, such as a smartphone device, a tablet device, or a laptop computer. In some embodiments, the sensor is wireless-enabled and is configured to communicate the measured health parameter wirelessly to the data processing machine.

While various exemplary embodiments of the invention have been described above, it should be understood that they have been presented by way of example only, and not by way of limitation. Likewise, the various figures or diagrams depict exemplary configurations of the invention, which are provided to illustrate various features and functionalities that can be provided by various embodiments of the invention. The invention is not restricted to the illustrated example architectures or configurations, but can be implemented using a variety of alternative architectures and configurations.

Additionally, it should be understood that the various features and functionalities described in connection with one or more individual embodiments are not limited in their applicability to the particular embodiment(s) with which they are described, but instead can be applied, alone or in some combination, to one or more other embodiments of the invention, whether or not such features are explicitly described as being a part of a described embodiment. Thus the breadth and scope of the present invention should not be limited by any of the above-described exemplary embodiments.

What is claimed is:

1. A bra, comprising:
a first cup configured to cover at least a portion of a first breast of a wearer; and
a second cup configured to cover at least a portion of a second breast of the wearer, wherein the second cup is detachably securable to the first cup,
wherein at least one of the first and second cups includes at least one pocket that is configured to house and secure a sensor for measuring a health parameter of the wearer, and wherein at least one of the first and second cups further comprises at least one window configured to allow at least a portion of a back surface of the sensor to contact the wearer's breast.

2. The bra of claim 1 wherein the at least one pocket is located at a lower portion of the second cup.

3. The bra of claim 1 wherein the at least one pocket comprises a front slot configured to allow a wire of the sensor to extend therethrough.

4. The bra of claim 1 wherein the at least one pocket includes a top flap configured to be detachably closed over a top opening of the at least one pocket.

5. The bra of claim 1, further comprising:
a back structure coupled to the first and second cups, wherein the back structure is configured to wrap around a back of the wearer to hold the bra in place.

6. The bra of claim 5, furthering comprising:
a first shoulder strap attached to the first cup and the back structure; and
a second shoulder strap attached to the second cup and the back structure.

7. The bra of claim 6, further comprising:
a first strap adjuster coupled to the first shoulder strap; and
a second strap adjuster coupled to the second shoulder strap.

8. The bra of claim 1, further comprising a clasp configured to secure a test lead coupled to the sensor.

9. A bra, comprising:
a first cup configured to cover at least a portion of a first breast of a wearer; and
a second cup configured to cover at least a portion of a second breast of the wearer, wherein the second portion is detachably securable to the first cup,
wherein at least the first cup is formed from a single piece of fabric, and wherein a surface area of the first cup is smaller than a surface area of the second cup such that when worn by the wearer the first cup facilitates a greater surface area of the first breast to be exposed compared to the second breast to allow for direct contact between the first breast and at least one health parameter sensor.

10. The bra of claim 9 wherein at least one of the first and second cups includes at least one pocket that is configured to house and secure a sensor for measuring a health parameter of the wearer.

11. The bra of claim 10 wherein the at least one pocket is located at a lower portion of the first cup.

12. The bra of claim 9, furthering comprising:
a back support portion that is configured to wrap around a back of the wearer to hold the bra in place.

13. The bra of claim 12, furthering comprising:
a first shoulder strap attached to the first portion and the back support portion; and
a second shoulder strap attached to the second portion and the back support portion, wherein the first and second shoulder straps, the back support portion, the first and second portions are continuously formed from the single piece of fabric.

14. The bra of claim 12, furthering comprising:
a single shoulder strap attached to the second cup and the back support portion, wherein the first cup is not coupled to the back support portion via a shoulder strap.

15. A health monitoring bra for measuring a health parameter of a patient, comprising:
a bra comprising a first cup configured to cover at least a portion of a first breast of a wearer and a second cup configured to cover at least a portion of a second breast of the wearer, wherein the second cup is detachably securable to the first cup,
wherein at least one of the first and second cups includes at least one pocket that is configured to house and secure at least one sensor, respectively, for measuring a health parameter of the wearer, and wherein at least one of the first and second cups further comprises at least one window configured to allow at least a portion of a back surface of the sensor to contact the wearer's breast; and
at least one sensor configured to be placed within the at least one pocket and measure the health parameter of the wearer.

16. The health monitoring bra of claim 15 wherein the at least one sensor comprises an EKG pad.

17. The health monitoring bra of claim 15 wherein the at least one sensor is wireless-enabled to communicate the health parameter data to a health parameter monitoring device.

18. The health monitoring bra of claim 17 wherein the health parameter monitoring device comprises a smartphone device programmed to process the health parameter data.

19. The health monitoring bra of claim 17 wherein the health parameter monitoring device comprises a tablet computing device.

* * * * *